United States Patent
Kraus et al.

(10) Patent No.: US 9,034,318 B2
(45) Date of Patent: May 19, 2015

(54) CHEMICALLY MODIFIED CYSTATHIONINE BETA-SYNTHASE ENZYME FOR TREATMENT OF HOMOCYSTINURIA

(71) Applicant: The Regents of the University of Colorado, a body corporate, Denver, CO (US)

(72) Inventors: Jan P Kraus, Littleton, CO (US); Tomas Majtan, Aurora, CO (US); Erez Bublil, Ets Efraim (IL)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 13/803,804

(22) Filed: Mar. 14, 2013

(65) Prior Publication Data

US 2014/0212403 A1    Jul. 31, 2014

Related U.S. Application Data

(60) Provisional application No. 61/758,138, filed on Jan. 29, 2013.

(51) Int. Cl.

| | |
|---|---|
| *A61K 38/54* | (2006.01) |
| *C12N 9/96* | (2006.01) |
| *C12N 9/88* | (2006.01) |
| *C07H 21/04* | (2006.01) |
| *C07K 1/00* | (2006.01) |
| *A61K 38/51* | (2006.01) |
| *A61K 45/06* | (2006.01) |
| *A61K 31/198* | (2006.01) |
| *A61K 31/205* | (2006.01) |
| *A61K 31/385* | (2006.01) |
| *A61K 9/00* | (2006.01) |

(52) U.S. Cl.
CPC . *C12N 9/96* (2013.01); *A61K 38/51* (2013.01); *A61K 45/06* (2013.01); *C12N 9/88* (2013.01); *C12Y 402/01022* (2013.01); *A61K 31/198* (2013.01); *A61K 31/205* (2013.01); *A61K 31/385* (2013.01); *A61K 9/0019* (2013.01)

(58) Field of Classification Search
CPC ........ C12N 15/8261; C12N 9/88; C12N 9/96; C12Y 402/01022; A61K 38/51; A61K 45/06
USPC ................. 424/94.3; 435/188, 232; 536/23.2; 530/350
See application file for complete search history.

(56) References Cited

U.S. PATENT DOCUMENTS

| | | |
|---|---|---|
| 5,523,225 A | 6/1996 | Kraus |
| 5,635,375 A | 6/1997 | Kraus et al. |
| 7,485,307 B2 * | 2/2009 | Kraus et al. ................ 424/192.1 |
| 8,007,787 B2 | 8/2011 | Kraus |

FOREIGN PATENT DOCUMENTS

| | | |
|---|---|---|
| EP | 1 396 537 A1 | 3/2004 |
| WO | 03106971 A2 | 12/2003 |
| WO | 2012001336 A1 | 1/2012 |
| WO | 2013148580 A1 | 10/2013 |

OTHER PUBLICATIONS

Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
El-Sayed et al., PLP-dependent enzymes: a potent therapeutic approach to cancer and cardiovascular diseases, Targets in gene therapy, Prof. Yongping You (Ed.), 307-540-2, In Tech, 2011.*
Meier et al., Structure of human cystathionine β-synthase: a unique pyridoxal 5'-phosphate-dependent hemeprotein. The EMBO Journal vol. 20 No. 15 pp. 3910-3916. 2001.*
Janosik et al., Crystallization and preliminary X-ray diffraction analysis of the active core of human recombinant human cystathionine β-synthase: an enzyme involved in vascular disease. Acta Cryst. D57, 289-291, 2001.*
Allen et al., 1993, "Serum betaine, N,N-dimethylglycine and N-methylglycine levels in patients with cobalamin and folate deficiency and related inborn errors of metabolism." Metabolism 42(11):1448-60.
Gaustadnes et al., 1999, "Prevalence of congenital homocystinuria in Denmark." N Engl J Med. 340(19):1513.
Jakubowski et al., 2008, "Mutations in cystathionine beta-synthase or methylenetetrahydrofolate reductase gene increase N-homocysteinylated protein levels in humans." FASEB J 22(12): 4071-6.
Kozich & Kraus, 1992, "Screening for mutations by expressing patient cDNA segments in *E. coli*: homocystinuria due to cystathionine beta-synthase deficiency." Hum. Mutation 1:113-23.
Kraus, 1987, "Cystathionine beta-synthase (human)." Methods Enzymol. 143:388-94.
Li & Stewart, 1999, "Homocystinuria and psychiatric disorder: a case report." Pathology 31(3):221-24.
Linnebank et al., 2001, "High prevalence of the I278T mutation of the human cystathionine beta-synthase detected by a novel screening application." Thromb Haemost. 85(6):986-88.

(Continued)

*Primary Examiner* — Ganapathirama Raghu
(74) *Attorney, Agent, or Firm* — McDonnell Boehnen Hulbert & Berghoff LLP

(57) ABSTRACT

The invention provides reagents and methods for enzyme replacement therapy using chemically modified species of human cystathionine β-synthase (CBS) to treat homocystinuria and other related diseases and disorders.

24 Claims, 4 Drawing Sheets

(56) References Cited

OTHER PUBLICATIONS

Figure 1:
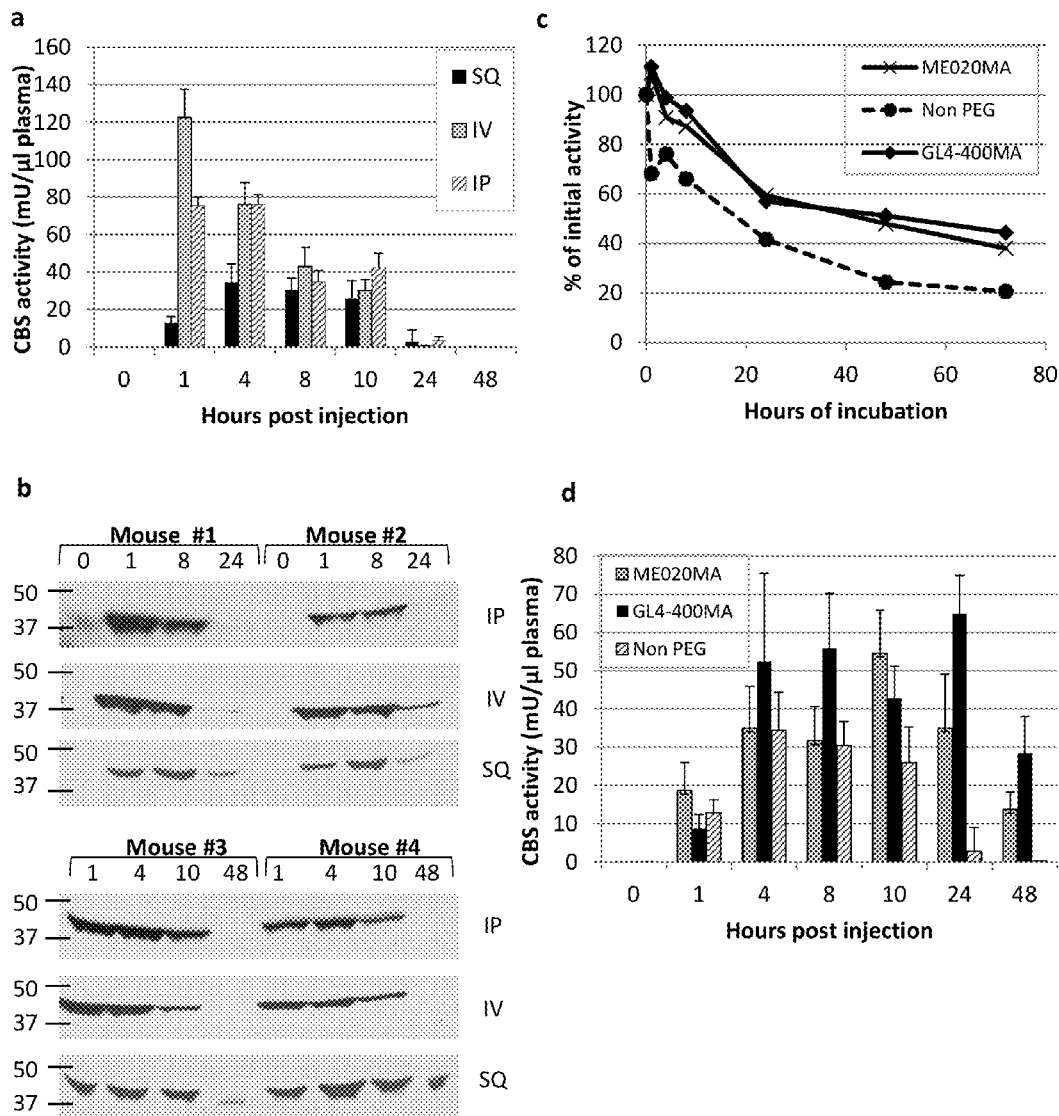

Linnebank et al., 2003, "Isolated thrombosis due to the cystathionine beta-synthase mutation c.833T>C (1278T)." J. Inherited Metabol. Dis. 26(5):509-11.

Lowry et al., 1951, "Protein measurement with the Folin phenol reagent." J. Biol. Chem. 193(1):265-75.

Maclean et al., 2002, "High homocysteine and thrombosis without connective tissue disorders are associated with a novel class of cystathionine beta-synthase (CBS) mutations." Hum. Mutat. 19(6):641-55.

Majtan et al., 2010, "Rescue of cystathionine beta-synthase (CBS) mutants with chemical chaperones: purification and characterization of eight CBS mutant enzymes." J Biol Chem. 285(21):15866-73.

Refsum et al., 2004, "Facts and recommendations about total homocysteine determinations: an expert opinion." Clin. Chem. 50:3-32.

Sokolova et al., 2001, "Cystathionine beta-synthase deficiency in Central Europe: discrepancy between biochemical and molecular genetic screening for homocystinuric alleles." Hum Mutat. 18(6):548-9.

Vargas et al., 1993, "Detection of c-type cytochromes using enhanced chemiluminescence." Anal. Biochem. 209 (2):323-6.

Wilcken et al., 1983, "Homocystinuria—the effects of betaine in the treatment of patients not responsive to pyridoxine." N. Engl. J. Med. 309(8):448-53.

Walter, et al., 1998, "Strategies for the treatment of cystathionine beta-synthase deficiency: the experience of the Willink Biochemical Genetics Unit over the past 30 years." Eur J Pediatr 157(Suppl 2): S71-6.

International Search Report from International Application No. PCT/US2014/013602, mailed on Jun. 17, 2014, pp. 1-6.

Frank et al., "Purification and characterization of the wild type and truncated human cystathionine beta-synthase enzymes expressed in *E.coli*" Archives of Biochemistry and Biophysics, 470(1): 64-72 (2007).

Harris & Chess "Effect of Pegylation on Pharmaceuticals" Nature Reviews. Drug Discovery 2(3):214-21 (2003).

Levy "Physician's Guide to The Homocystinurias" published by the National Organization for Rare Disorders, pp. 1-8 (2010).

Taoka et al., "Assignment of enzymatic functions to specific regions of the PLP-dependent heme protein cystathionine beta-synthase." Biochemistry 38(40):13155-61 (1999).

Tan et al., "Polyethylene Glycol Conjugation of Recombinant Methionase for Cancer Therapy," Protein Expression and Purification 12:45-52 (1998).

* cited by examiner

CHEMICALLY MODIFIED CYSTATHIONINE BETA-SYNTHASE ENZYME FOR TREATMENT OF HOMOCYSTINURIA

CROSS-REFERENCE TO RELATED APPLICATIONS

This application is a non-provisional application of U.S. Provisional Application No. 61/758,138, filed Jan. 29, 2013; and is related to U.S. Pat. No. 7,485,307, filed Jun. 17, 2002, U.S. Pat. No. 8,007,787, filed Jan. 24, 2009, and U.S. application Ser. No. 13/221,379, filed Aug. 30, 2011, the disclosure of each of which is incorporated by reference.

FIELD OF THE INVENTION

The present invention generally relates to enzyme replacement therapy using modified human Cystathionine Beta-Synthase (CBS) to significantly reduce serum homocysteine (Hcy) concentrations and increase the concentration of the downstream metabolites such as cystathionine and cysteine, which can be used for treatment of diseases such as homocystinuria and homocysteine remethylation disorders.

BACKGROUND OF THE INVENTION

CBS, a central enzyme in the transsulfuration pathway, plays an essential role in homocysteine (Hcy) metabolism in eukaryotes (Mudd et al., 2001, in THE METABOLIC AND MOLECULAR BASES OF INHERITED DISEASE, 8 Ed., pp. 2007-2056, McGraw-Hill, New York). CBS catalyzes Hcy condensation with L-serine to form cystathionine. When CBS activity is dramatically reduced or absent, as a result of certain genetic mutations, Hcy builds up in tissues and blood. The CBS enzyme catalyzes a pyridoxal-5'-phosphate (PLP; Vitamin $B_6$)-dependent condensation of serine and homocysteine to form cystathionine, which is then used to produce cysteine by another PLP-dependent enzyme, cystathionine γ-lyase. In mammalian cells that possess the transsulfuration pathway, CBS occupies a key regulatory position between the remethylation of Hcy to methionine or its alternative use in the biosynthesis of cysteine.

In healthy normal individuals, CBS-mediated conversion of Hcy to cystathionine is the rate-limiting intermediate step of methionine (Met) metabolism to cysteine (Cys). Vitamin $B_6$ is an essential coenzyme for this process. In patients with certain genetic mutations in the CBS enzyme, the conversion of Hcy to cystathionine is slowed or absent, resulting in elevations in the serum concentrations of the enzymatic substrate (Hcy) and a corresponding decrease in the serum concentrations of the enzymatic product (cystathionine). The clinical condition of an elevated serum level of Hcy, and its concomitant excretion into the urine, is collectively known as homocystinuria.

The estimates on the prevalence of homocystinuria vary widely. Data from newborn screening and clinical ascertainment provide a range of 1:200,000 to 1:335,000 live births (Mudd et al., 2001). Recent evidence from DNA screening studies of newborns in Denmark, Germany, Norway and the Czech Republic found that the true incidence may be as high as ~1:6,000 (Gaustadnes et al., 1999, *N Engl J Med.* 1340: 1513; Linnebank et al., 2001, *Thromb Haemost.* 85:986; Refsum et al., 2004, *Clin. Chem.* 50:3; Sokolova et al., 2001, *Hum Mutat.* 18:548). Additionally, recent work has indicated that CBSDH patients exist with either psychiatric or cardiovascular complications but are currently undiagnosed due to a lack of the characteristic connective tissue defects that are typically instrumental in diagnosis (Li and Stewart, 1999, *Pathol.* 31:221; Linnebank et al., 2003, *J. Inherited Metabol. Dis.* 26: 509; Maclean et al., 2002, *Hum Mutat.* 19:641). The primary health problems associated with CBS-deficient homocystinuria (CBSDH) include: cardiovascular disease with a predisposition to thrombosis, resulting in a high rate of mortality in untreated and partially treated patients; connective tissue problems affecting the ocular system with progressive myopia and lens dislocation; connective tissue problems affecting the skeleton characterized by marfanoid habitus, osteoporosis, and scoliosis; and central nervous system problems, including mental retardation and seizures.

The therapeutic resolution of CBS-associated homocystinuria is dependent upon the type of mutations present in the CBS gene. Approximately 160 pathogenic mutations of the CBS gene have been identified to date in humans. There is a functional trichotomy in the nature of pathogenic mutations associated with CBSDH. One group of mutations is classified as "pyridoxine-responsive," where CBS enzyme function can be restored by high dose Vitamin $B_6$ therapy. This treatment can be effective, but does not always mitigate the pathological events in these patients, and some of the events occur even in these patients over time. The second group of functional mutations is represented by the "C-terminal CBS mutants" that are defective in their ability to respond to post-translational up-regulation by S-adenosylmethionine. Patients with this class of mutations usually lack the mental retardation and connective tissue aspects of the phenotype. This class is detected after measurement of plasma Hcy levels following an idiopathic thrombotic event before the age of 40 years (Maclean et al., 2002, *Hum Mutat.* 19: 641-55). The final group of CBSDH mutations is "classical homocystinuria," which represents the most severe form of the disease. For these latter two groups of patients, Vitamin $B_6$ therapy in isolation does not effectively lower serum Hcy levels.

The pathophysiology of homozygous CBS deficiency is undoubtedly complex, but there is a consensus that the fundamental instigator of end-organ injury is an extreme elevation of serum Hcy. The toxicity of profound elevations in blood and tissue concentrations of Hcy may ensue from the molecular reactivity and biological effects of Hcy per se or from its metabolites (e.g., Hcy-thiolactone) that affect a number of biological processes (Jakubowski et al., 2008, *FASEB J* 22: 4071-6). Abnormalities in chronic platelet aggregation, changes in vascular parameters, and endothelial dysfunction have all been described in patients with homocystinuria.

Currently, three treatment options exist for the treatment of CBSDH:
1) Increase of residual activity of CBS activity using pharmacologic doses of Vitamin $B_6$ in Vitamin $B_6$-responsive patients;
2) Lowering of serum Hcy by a diet with a strict restriction of the intake of Met; and
3) Detoxification by betaine-mediated conversion of Hcy into Met, thus lowering serum Hcy concentration.

Each of these three therapies is aimed at lowering serum Hcy concentration. The standard treatment for individuals affected with Vitamin $B_6$ non-responsive CBSDH consists of a Met-restricted diet supplemented with a metabolic formula and Cys (which has become a conditionally essential amino acid in this condition). Intake of meat, dairy products and other food high in natural protein is prohibited. Daily consumption of a poorly palatable, synthetic metabolic formula containing amino acids and micronutrients is required to prevent secondary malnutrition. Supplementation with betaine (tradename: CYSTADANE, synonym: trimethylglycine) is also a standard therapy. Betaine serves as a methyl donor for the remethylation of Hcy to Met catalyzed by betaine-homocysteinemethyltransferase in the liver (Wilcken et al., 1983, *N Engl J Med* 309: (8), 448-53). Dietary compliance generally has been poor, even in those medical centers where optimal care and resources are provided, and this noncompliance has major implications on the development of life-threatening complications of homocystinuria.

The evidence described in the above sections is summarized in the following points:

Untreated homocystinuria has a high rate of complications in the vasculature, connective tissue, and central nervous system.

Treatments that lower serum Hcy, such as a severely Met-restricted diet and betaine, lower the associated clinical problems if executed well. Improvements in cognitive performance require treatment initiation in early infancy.

Compliance with diet is uniformly poor. In patients initiating therapy in the neonatal period, the loss of compliance occurs in adolescence. In patients beginning therapy after the neonatal period, compliance is abysmal at all ages. The extreme difficulties of the current treatment approach are most readily evident in patients who experience life-threatening symptoms preventable by diet, and yet are unable to adhere to this treatment.

Failure of dietary compliance causes increased serum Hcy, resurgence of complications in the vascular and connective tissue including fatal and incapacitating events, and risks severe side-effects such as cerebral edema (from excessive serum Met concentration) or severe malnutrition (from lack of essential amino acids).

The most effective therapeutic strategy is to increase enzyme activity, as is evident when given pyridoxine to Vitamin $B_6$ responsive homocystinuria. This strategy is not possible for Vitamin $B_6$ non-responsive patients due to the mutation status, and increased enzyme activity in these patients will depend on the delivery of exogenous enzyme, i.e. enzyme replacement therapy (ERT) (a strategy that has never been attempted for treating homocystinuria).

Of the three current treatment strategies with demonstrated efficacy: (1) increasing enzyme activity with pyridoxine in Vitamin $B_6$ responsive patients; (2) reducing accumulating metabolites by a Met-restricted diet; and (3) detoxification by enzyme activity of the betaine-homocysteine methyltransferase in betaine treatment, all have in common a lowering of total Hcy in plasma (Walter, et al., 1998, *Eur J Pediatr* 157(Suppl 2): S71-6).

In addition, for all current treatment strategies (except B6 supplementation, which is appropriate for only a subset of homocystinurics), reduction in homocysteine is not accompanied by increases in cystathionine or cysteine. Because it has not been established that excess homocysteine, rather than a deficiency of a downstream metabolite, is responsible for clinical symptoms, treatment strategies that are limited to reducing homocysteine may be inadequate for providing robust and effective treatment options.

Thus, there remains a need in the art for more effective treatment strategies for patients with homocystinuria.

SUMMARY OF THE INVENTION

As set forth herein, the invention provides compositions, specifically pharmaceutical compositions, and methods for reducing serum Hcy in patients with homocystinuria. Also provided are compositions, specifically pharmaceutical compositions, which restore substantially normal levels of metabolites including but not limited to methionine, such as cysteine and cystathionine. As described more specifically herein, reagents and methods for enzyme replacement therapy (ERT) for homocystinuria are provided wherein a truncated form of the natural enzyme has been recombinantly engineered to provide improved stability, activity, and medicinal utility in vivo. More specifically, the invention provides an engineered variant of human CBS that constitutes a truncated recombinant human CBS (r-hCBSΔC) homodimeric enzyme wherein the C-terminal regulatory region has been removed (SEQ ID NO: 3). In the particular embodiments disclosed herein, species of the truncated recombinant human CBS are chemically modified, particularly by covalent attachment of polyethyleneglycol (PEG) moieties of r-hCBSΔC (herein termed "the PEGylated species"). These reagents and methods enable patients with homocystinuria, to enjoy a far less restrictive diet (e.g., daily intake of 2 g or more of protein per kg), and have significantly decreased Hcy plasma levels and substantially normal metabolite levels including but not limited to methionine, such as cysteine and cystathionine, leading in the long-term to clinical improvement.

The invention advantageously enables patients to achieve good control of serum Hcy levels without the use of an extremely restricted diet, which has an unacceptable noncompliance rate. All current clinical and preclinical data relate improvement in clinical symptomatology to achievement of control of homocysteine, the core metabolite in this inborn error of metabolism. Use of the PEGylated species maybe advantageously accompanied by improved compliance, improved patient metabolism, and hence improved clinical outcomes as reflected in decreased incidence of morbidity and mortality, associated inter alia with significantly reduced serum Hcy concentrations.

As disclosed herein, the PEGylated species advantageously have an increased size compared with the non-PEGylated r-hCBSΔC, wherein there is reduced or delayed clearance of the PEGylated species. In addition, chemical modification with PEG masks potential immunogenic epitopes on the surface of a protein and hinders access to the protein for proteolytic enzymes. Pegylation also advantageously alters the physico-chemical properties of the r-hCBSΔC protein, thus modifying its biodistribution, stability, and solubility without significantly detracting from its potency.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS OF THE INVENTION

The following detailed description of the embodiments of the present invention can be best understood when read in conjunction with the following drawings.

FIG. 1 illustrates experimental evidence for enhancement in plasma enzyme retention time in vivo and enzymatic activity in vitro following rhCBSΔC PEGylation. FIG. 1*a* is a bar graph showing the results of experiments wherein C57BL/6J mice were injected with 5 mg/kg body weight of the human truncated CBS (rhCBSΔC) via intra-peritoneal (IP), intra-vascular (IV) or sub-cutaneous (SQ) routes. Two experimental groups (denoted 1 and 2) of 5 mice each were used for each injection route (total n=30). For each injection route, blood was collected from group 1 at 0, 1, 8 and 24 hours post injection and from group 2 at 1, 4, 10, and 48 hours post injection. Plasma was analyzed for CBS activity using the radiometric activity assay (as described in Example 1). FIG. 1b is a photograph of the results of Western blot analysis of CBS in plasma from two representative mice of each group as described in FIG. 1a to follow CBS clearance from circulation. FIG. 1c is a graph showing the results of experiments where the rhCBSΔC enzyme was PEGylated with ME020MA or GL4-400MA PEGs as described in Example 2 and incubated in mouse plasma at 37° C. (final concentration 160 ng/ul). Samples were taken at the indicated time points and activity was compared to the non-PEGylated enzyme using the radiometric activity assay (further as described in Example 1c). FIG. 1d is a bar graph showing the results of experiments where mice were injected with 5 mg/kg body weight of ME020MA- or GL4-400MA-PEGylated rhCBSΔC or with non-PEGylated rhCBSΔC via SQ route. Each treatment arm consisted of two groups of 5 mice and bled as described in Example 2 and shown in FIG. 1A (total 30 mice). Plasma was analyzed for CBS activity using the radiometric activity assay.

Figure 2:
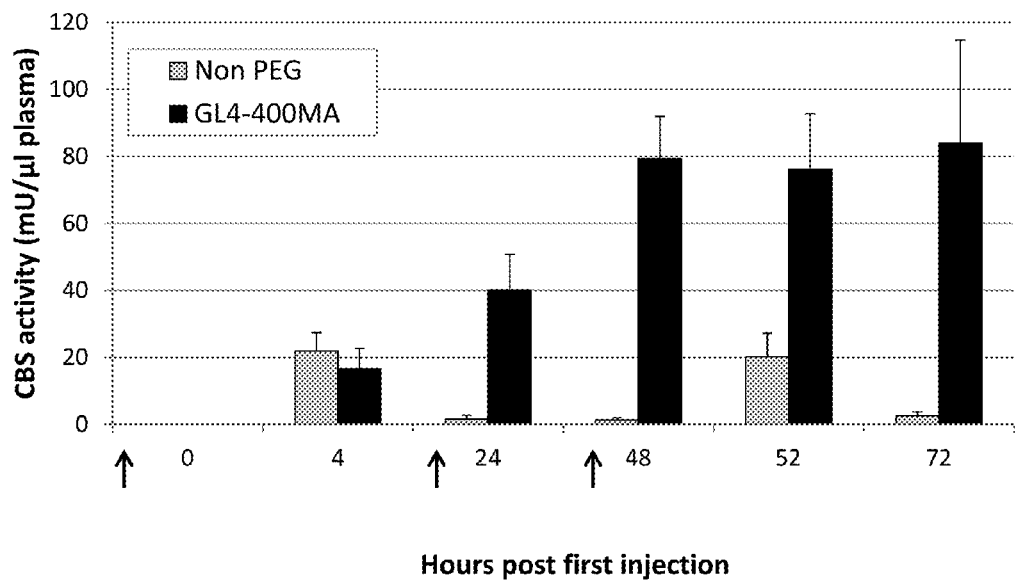

FIG. 2 is a bar graph showing the results of experiments performed by repeated injection regimen. Injection with the PEGylated, but not with the non-PEGylated rhCBSΔC, exhibits buildup of CBS activity in vivo. C57BL/6J mice were injected at 0, 24, 48 hours (arrows) with 5 mg/kg body weight of non-PEGylated rhCBSΔC (n=5) or with GL4-400MA rhCBSΔC (n=5) and bled at the indicated time points. Plasma was analyzed for CBS activity using the radiometric activity assay described in Example 1c.

Figure 3:
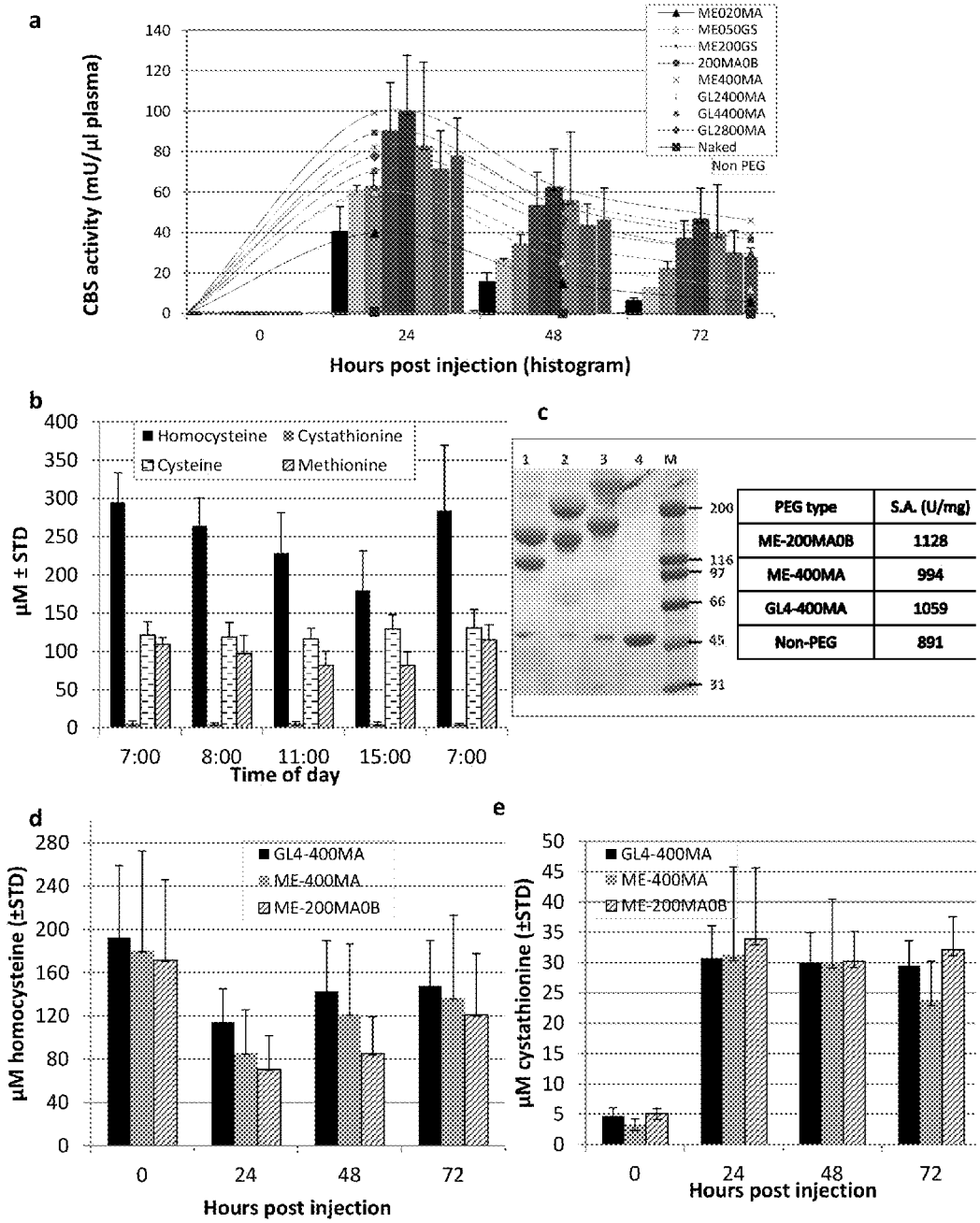

FIG. 3 illustrates experimental evidence that single injection of the PEGylated rhCBSΔC reduces homocysteine and increases cystathionine in plasma. FIG. 3a is a graph showing the results of experiments wherein twenty seven C57BL/6J mice were divided into 9 experimental groups (n=3). Each experimental group was injected via SQ route with 5 mg/kg body weight of rhCBSΔC PEGylated with the indicated PEG molecule, or injected with non-PEGylated enzyme. Blood samples were drawn at the indicated time points and CBS enzyme activity was determined using radiometric activity assay as described in Example 1c. Data is presented as a histogram with standard deviation (STD), and as a scatter plot. FIG. 3b is a bar graph showing the results of experiments wherein blood from 6 HO mice (Maclean et al., 2010, *Mol. Genet. Metab.* 101: 153-62) was drawn at the indicated time points throughout a 24-hour cycle. Plasma metabolites levels were determined by Stable-Isotope-Dilution Liquid Chromatography-Mass Spectrometry for each time point as described in Example 1f.

FIG. 3c is a photograph of the results of electrophoretic analysis of rhCBSΔC PEGylated with ME-400MA (lane 1), GL4-400MA (lane 2) or ME-200MA0B (lane 3) resolved by electrophoresis along with non-PEGylated enzyme (lane 4), and stained with Coomassie blue. The specific activity (S.A.) for each of the PEGylated and non-PEGylated rhCBSΔC is indicated in the Table.

FIGS. 3d and 3e are bar graphs showing the results of experiments wherein HO mice were injected once at time 0 with rhCBSΔC that had been PEGylated with the indicated PEG molecules, and bled at times 0 (prior to injection), 24, 48 and 72 hours post injection. Levels of plasma homocysteine (d) and cystathionine (e) for each of the groups (n=5-6) are indicated.

Figure 4:
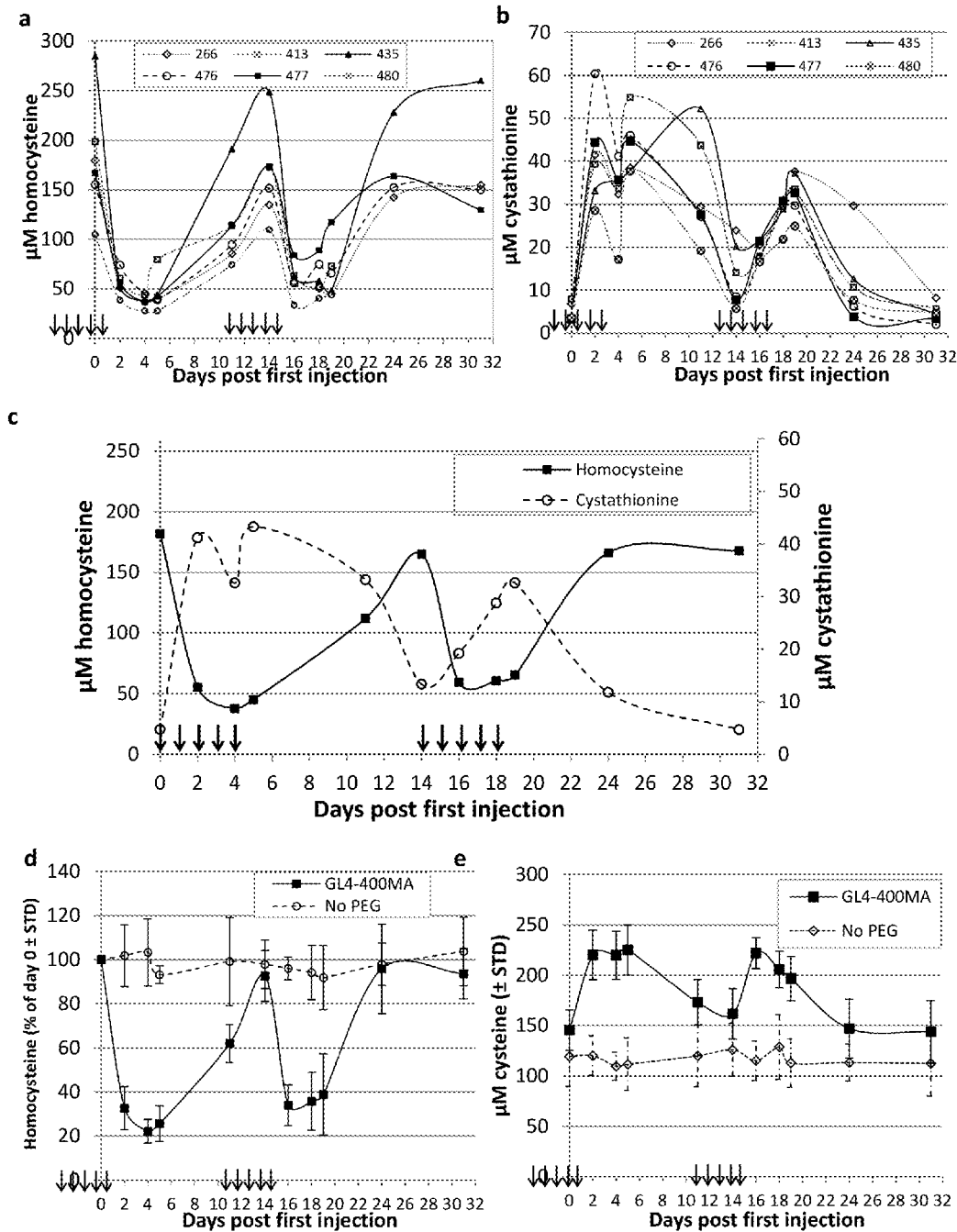

FIG. 4 illustrates experimental evidence that repeated injection of the PEGylated rhCBSΔC significantly impacts homocysteine and cystathionine plasma levels, and restores normal cysteine levels. Six HO mice were injected with rhCBSΔC PEGylated with GL4-400MA PEG, on days 0, 1, 2, 3 and 4, and then again on days 14, 15, 16, 17 and 18 (indicated by the arrows). Plasma samples were drawn (always prior to injection) at the indicated time points. For comparison, same injection regimen was carried out in 5 HO mice injected with the non-PEGylated enzyme. Plasma metabolite levels were determined as described in Example 1f. FIG. 4a is a graph showing results for homocysteine and cystathionine FIG. 4b is a graph showing results for plasma concentrations for each individual HO mouse. FIG. 4c is a graph showing average concentrations of homocysteine and cystathionine in plasma from the treated HO mice. FIG. 4d is a graph showing the effect of the PEGylated rhCBSΔC on plasma homocysteine levels as compared to non-PEGylated rhCBSΔC (presented as percentage of time 0). FIG. 4e is a graph showing the effect of PEGylated rhCBSΔC on plasma cysteine levels as compared to non-PEGylated rhCBSΔC.

DETAILED DESCRIPTION

Provided herein are compositions, specifically pharmaceutical compositions, and methods for treating patients with homocystinuria, for example, by enzyme replacement therapy (ERT).

The nucleic acid sequence encoding human CBS and the amino acid sequence encoded thereby are available through GenBank Accession No. L19501, and these sequences are also disclosed in U.S. Pat. No. 5,523,225, which is incorporated herein by reference in its entirety. The coding sequence for CBS is represented herein as SEQ ID NO: 1, and is a nucleic acid sequence encoding SEQ ID NO: 2, which is the amino acid sequence for full-length human CBS, having 551 amino acid residues. The nucleic acid sequence of the genomic DNA encoding CBS is also publicly available through sequence databases such as Genbank and at University of Colorado-Denver webpage under Kraus Lab.

As used herein, an isolated protein or polypeptide in the invention is specifically a truncated version of isolated cystathionine β-synthase protein (CBS protein), particularly human CBS protein. Such a CBS protein can include, but is not limited to, purified truncated CBS protein, chemically cleaved and recombinantly produced truncated CBS protein, and isolated CBS protein associated with other proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. An isolated truncated CBS protein of the present invention can be produced recombinantly in cells, for example bacterial cells. In addition, and by way of example, a "human truncated CBS protein" refers to a truncated CBS protein (as set forth herein) from a human (*Homo sapiens*) or to a CBS protein that has been otherwise produced from the knowledge of the structure (e.g., sequence) and perhaps the function of a naturally occurring CBS protein from *Homo sapiens*. In other words, a human truncated CBS protein includes biologically active, truncated human CBS protein as described in detail herein.

As used herein, the term "homologue" (or variant or mutant) is used to refer to a protein or peptide which differs from a naturally occurring protein or peptide (i.e., the "prototype" or "wild-type" protein) by modifications to the naturally occurring protein or peptide, but which maintains the basic protein and side chain structure of the naturally occurring form. Such changes include, but are not limited to: changes in one, few, or even several amino acid side chains; changes in one, few or several amino acids; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, changed, or essentially similar properties as compared to the naturally occurring protein or peptide. In particular embodiments, the invention provides truncated CBS proteins having C-terminal deletions of the naturally occurring CBS protein.

Methods to measure protein expression levels of CBS according to the invention include, but are not limited to Coomasie blue or silver staining of protein in a separation media, such as gel electrophoresis, Western blotting, immunocytochemistry, other immunologic-based assays; assays based on a property of the protein including but not limited to, enzyme assays, ligand binding or interaction with other protein partners. Binding assays are also well known in the art. For example, a BIAcore instrument can be used to determine the binding constant of a complex between two proteins. The dissociation constant for the complex can be determined by monitoring changes in the refractive index with respect to time as buffer is passed over the chip. Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

In certain aspects, a CBS variant can include any combination of the N-terminal deletions or modifications and the C-terminal deletions described herein or in U.S. Pat. No. 8,007,787, incorporated by reference herein. In another embodiment additional modifications can be achieved by modification of other amino acid residues to provide a given percent identity to the wild-type CBS sequence. In particular embodiments, the human CBS variant of the invention is a truncated recombinant human CBS (r-hCBSΔC) homodimeric enzyme wherein the C-terminal regulatory region has been removed (SEQ ID NO: 3).

In another aspect of the invention, any of the CBS variants described herein has no more than one or two non-CBS amino acid residues at the N-terminus (i.e., the variant comprises no more than one or two amino acid residues at the N-terminus that is/are not a residue of the naturally occurring human cystathionine β-synthase amino acid sequence at that position). Such a variant can be produced, for example, using the novel method of recombinant CBS production described below.

In a further aspect, any of the above-described CBS variants of the present invention, including any truncated CBS protein, comprises an amino acid sequence that is at least about 60% identical, or at least about 65% identical, or at least about 70% identical, or at least about 75% identical, or at least about 80% identical, or at least about 85% identical, or at least about 90% identical, or at least about 95% identical, or at least about 96% identical, or at least about 97% identical, or at least about 98% identical, or at least about 99% identical, to the wild-type amino acid sequence represented by SEQ ID NO:2, or to a biologically active truncation thereof (including non-heme-binding, but catalytically active variants). In particular embodiments, the human CBS variant of the invention is a truncated recombinant human CBS (r-hCBSΔC) homodimeric enzyme wherein the C-terminal regulatory region has been removed (SEQ ID NO: 3).

In certain aspects, a CBS protein of the present invention comprises an amino acid sequence that is less than 100% identical to SEQ ID NO: 2, particularly truncated embodiments thereof having an amino acid sequence of the truncation variants as set forth in U.S. Pat. No. 8,007,787 and particularly SEQ ID NO: 3 set forth herein, and in specific embodiments having less than 99% sequence identity, less than 98% sequence identity, less than 97% sequence identity, less than 96% sequence identity, less than 95% sequence identity, less than 94% sequence identity, less than 93% sequence identity, less than 92% sequence identity, less than 91% sequence identity, less than 90% sequence identity, and so on, in increments of whole integers, to SEQ ID NO: 2 and truncated variants thereof having an amino acid sequence of the truncation variants as set forth in U.S. Pat. No. 8,007,787 and particularly SEQ ID NO: 3 set forth herein.

As used herein, unless otherwise specified, reference to a percent (%) identity refers to an evaluation of homology which is performed using a sequence alignment tool or program, including but not limited to (1) a BLAST 2.0 Basic BLAST homology search using blastp for amino acid searches and blastn for nucleic acid searches with standard default parameters, wherein the query sequence is filtered for low complexity regions by default; (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using anyone of these programs.

CBS derivatives are included in the scope of the present invention. Such derivatives are chemically modified CBS polypeptide compositions in which CBS polypeptide is linked to a polymer. The polymer selected is typically water-soluble so that the protein to which it is attached does not precipitate in an aqueous environment, such as a physiological environment. The polymer may be of any molecular weight, and may be branched or unbranched. Included within the scope of CBS polypeptide polymers is a mixture of polymers. In specific embodiments, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran (such as low molecular weight dextran, of, for example about 6 kDa), cellulose, or other carbohydrate based polymers, poly-(N-vinyl pyrrolidone) polyethylene glycol, propylene glycol homopolymers, a polypropylene oxide/ethylene oxide co-polymer, polyoxyethylatedpolyols (e.g., glycerol), polysalicylic acid, and polyvinyl alcohol. Also encompassed by the invention are bifunctional PEG crosslinking molecules that may be used to prepare covalently attached CBS polypeptide multimers.

In particular embodiments, the invention provides a truncated recombinant human CBS (r-hCBSΔC) homodimeric enzyme wherein the C-terminal regulatory region has been removed (SEQ ID NO: 3) that has been chemically modified by covalent linkage with polyethylene glycol (PEG), comprising the "PEGylated species" set forth herein. Specific embodiments of said PEGylated species are identified in Table 1.

Pegylation of CBS polypeptides may be carried out by any of the pegylation reactions known in the art. Pegylation may be carried out via an acylation reaction or an alkylation reaction with a reactive polyethylene glycol molecule (or an analogous reactive water-soluble polymer) as described below. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof.

One water-soluble polymer for use herein is polyethylene glycol, abbreviated PEG. As used herein, polyethylene glycol is meant to encompass any of the forms of PEG that have been used to derivatize other proteins, such as mono-($C_1$-$C_{10}$) alkoxy- or aryloxy-polyethylene glycol.

In general, chemical derivatization may be performed under any suitable conditions used to react a biologically active substance with an activated polymer molecule. Methods for preparing PEGylated CBS polypeptides will generally comprise the steps of (a) reacting the polypeptide with polyethylene glycol (such as a reactive ester, amine, aldehyde or maleimide derivative of PEG) under conditions whereby CBS polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-PEGylated product. In one particular aspect, the CBS polypeptide derivative will have a single PEG moiety at the amino terminus. In particular embodiments, the PEGylated CBS enzyme provided by the invention has an average of about 1 to about 10, more particularly 2 to about 5 and more particularly 3 to 5 PEG molecules covalently attached to each enzyme subunit in the composition.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with an CBS protein (including homologues) when it is used in a method disclosed by the present invention. Such methods include enzymatic reactions (e.g., production of cystathionine), preparation of therapeutic compositions, administration in a therapeutic composition, and all other methods disclosed herein. A "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the CBS protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition. In embodiments of the CBS proteins or truncated variants thereof produced in recombinant bacteria, the terms "purified" or "substantially pure" will be understood to encompass purification from lipopolysaccharides and other pyrogenic compounds.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of posttranslational modifications. Additionally, the promoter sequence might be genetically engineered to improve the level of expression as compared to the native promoter.

Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

One aspect of the present invention relates to a method to recombinantly produce and purify a human cystathionine beta-synthase. The method includes the step of cloning a nucleic acid sequence encoding a human CBS enzyme or a truncated variant thereof as set forth in U.S. Pat. No. 8,007,787 and specifically in SEQ ID NO: 4 herein into an expression vector. In certain embodiments the human CBS-encoding sequence has been modified to utilize codons optimized for expression in a microorganism such as *E. coli*. In other embodiments the vector includes: (a) a cloning site that will link a fusion partner (e.g., glutathione S-transferase, or GST) to the nucleic acid sequence to be expressed, and (b) a protease cleavage recognition site for the human rhinovirus 3C protease (e.g., available from GE Healthcare as a fusion protein called PreScission protease) or for a protease using a similar cleavage site, for cleaving the fusion partner from the CBS protein after expression of the recombinant fusion protein. As part of the invention, the expression vector is first genetically modified for the specific introduction of a CBS-encoding nucleic acid sequence which will result in expression of a CBS-fusion protein that can be cleaved by the human rhinovirus 3C protease such that a CBS protein having only one additional non-CBS, N-terminal amino acid residue is produced. This result is not possible using the unmodified multiple cloning site in the commercially available vector. The CBS-encoding nucleic acid sequence is introduced into the genetically modified vector, the recombinant fusion protein is expressed and purified using conventional methods or those suitable for CBS production (see e.g. U.S. Pat. No. 5,635,375, supra), and finally, the fusion partner and all but one of the non-CBS amino acid residues is cleaved from the CBS protein, leaving a highly purified, nearly completely human recombinant CBS protein which is ideal for use in human therapeutic applications. In particularly advantageous embodiments, the nucleotide encoding human CBS protein is engineered to the codon usage frequency of the recombinant cell in which it is recombinantly made. A non-limiting example of such an embodiment is set forth herein as SEQ ID NO: 4, wherein the CBS-encoding nucleic acid has been adapted for optimum recombinant expression in *E. coli*.

Some aspects of the present invention include a composition comprising any of the CBS variants described herein for in vitro cystathionine or cysteine production, to remove or produce hydrogen sulfide in vitro, or for therapeutic uses in vivo (e.g., to treat or prevent homocystinuria and conditions related thereto). Therefore, another embodiment of the invention relates to a composition comprising an isolated CBS protein and in particular a truncated variant thereof as set forth in U.S. Pat. No. 8,007,787 and specifically in SEQ ID NO: 3 herein. The composition typically also includes a pharmaceutically acceptable carrier. The compositions and their components can be used in any of the in vitro or therapeutic embodiments of the invention described herein.

As used herein, "HO" mice are a new mouse model of classical homocystinuria in which the mouse cbs gene is inactivated and that exhibits low-level expression of the human CBS transgene under the control of the human CBS promoter. This mouse model exhibits severe elevations in both plasma and tissue levels of Hcy, methionine, S-adenosylmethionine, and S-adenosylhomocysteine and a concomitant decrease in plasma and hepatic levels of cysteine. See Maclean et al., 2010 *Mol. Genet. Metab.* 101:153-62).

Compositions of the present invention are useful for producing cystathionine and cysteine in vitro or for treating a patient that will benefit from increased CBS activity (e.g., a patient with homocystinuria).

According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where it is desirable to regulate CBS activity. Pharmaceutically acceptable carriers are capable of maintaining a protein or recombinant nucleic acid molecule of the present invention in a form that, upon arrival of the protein or recombinant nucleic acid molecule at the target cell or tissue in a culture or in patient, the protein or recombinant nucleic acid molecule is capable of interacting with its target (e.g., a substrate for CBS).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other carriers of the present invention include liquids that, upon administration to a patient, form a solid or a gel in situ. In specific embodiments, carriers are also biodegradable (i.e., bioerodible). When the compound is a recombinant nucleic acid molecule, suitable carriers include, but are not limited to liposomes, viral vectors or other carriers, including ribozymes, gold particles, poly-L-lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a protein of the present invention at that site. A pharmaceutically acceptable carrier that is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Alternatively, said pharmaceutically acceptable carriers can comprise agents suitable for delivering said CBS proteins to an animal, preferably a human, in blood plasma or serum. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In specific embodiments, liposomes of the present invention include those liposomes commonly used in, for example, protein delivery methods known to those of skill in the art. Complexing a liposome with a protein of the present invention can be achieved using methods standard in the art.

Another embodiment of the present invention relates to a method to regulate biological processes, including cystathionine production, by regulating the expression and/or activity of CBS. This embodiment can generally include the use (e.g., administration) of therapeutic compositions comprising one or more of the CBS variants, particularly truncated CBS variants thereof as set forth in U.S. Pat. No. 8,007,787 and specifically in SEQ ID NO: 3 herein that are useful in a method of regulating the production of cystathionine that are mediated by or associated with the expression and biological activity of CBS.

Accordingly, in one embodiment, the method of the present invention regulates cystathionine production in an animal or human patient, wherein patient is protected from or treated for a disease that is amenable to regulation of cystathionine production, such as homocystinuria and conditions/symptoms related thereto (e.g., dislocated optic lenses, skeletal disorders, mental retardation and premature arteriosclerosis and thrombosis). As used herein, the phrase "protected from a disease" refers to reducing the symptoms of the disease; reducing the occurrence of the disease, and/or reducing the severity of the disease. Protecting a patient can refer to the ability of a therapeutic composition of the present invention, when administered to a patient, to prevent a disease from occurring and/or to cure or to treat the disease by alleviating disease symptoms, signs or causes. As such, to protect a patient from a disease includes both preventing disease occurrence (prophylactic treatment) and treating a patient that has a disease or that is experiencing initial symptoms or later stage symptoms of a disease (therapeutic treatment). The term, "disease" refers to any deviation from the normal health of a patient and includes a state when disease symptoms are present, as well as conditions in which a deviation (e.g., in non-limiting examples including infection, gene mutation, and genetic defect, etc.) has occurred, but symptoms are not yet manifested (e.g., a predisease condition).

More specifically, a therapeutic composition as described herein, when administered to a patient by the method of the present invention, preferably produces a result which can include alleviation of the disease (e.g., reduction of at least one symptom or clinical manifestation of the disease), elimination of the disease, alleviation of a secondary disease resulting from the occurrence of a primary disease, or prevention of the disease. In an additional aspect, administration of the therapeutic composition can produce a result that can include increased accumulation of downstream metabolites of transsulfuration in a mammal.

According to the present invention, an effective administration protocol (i.e., administering a therapeutic composition in an effective manner) comprises suitable dose parameters and modes of administration that result in the desired effect in the patient (e.g., an increase in the activity of cystathionine β-synthase in the patient or an increase in the condensation of serine and homocysteine to form cystathionine, preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in regulation of CBS activity or formation of cystathionine or cysteine in a patient, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration.

In one aspect of the invention, a suitable single dose of a therapeutic composition of the present invention is an amount that, when administered by any route of administration, regulates at least one parameter of CBS expression or biological activity in the cells of the patient as described above, as compared to a patient which has not been administered with the therapeutic composition of the present invention (i.e., a pre-determine control patient or measurement), as compared to the patient prior to administration of the composition, or as compared to a standard established for the particular disease, patient type and composition. The administered therapeutic composition is enzymatically active for an extended period of time. This period of time preferably exceeds 24 hours. The chemically modified therapeutic composition retains 70% or more of the initial activity of the administered composition after 24 hours. More preferably the period of enzymatic effective activity of the administered therapeutic composition exceeds 48 hours. Even more preferably the period of effective enzymatic activity of the administered therapeutic composition exceeds 72 hours. In certain aspects, the therapeutic composition may be administered several (e.g., twice or three or more) times per day or less frequently, including but not limited to weekly, biweekly, monthly, bimonthly or less frequently. In another aspect of the invention, a suitable dose of the therapeutic composition of the invention can administered in conjunction with betaine (such as CYSTADANE), a much relaxed protein restricted diet, an anti-coagulant, or a statin.

As discussed above, a therapeutic composition of the present invention is administered to a patient in a manner effective to deliver the composition to a cell, a tissue, and/or systemically to the patient, whereby the desired result is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based, protein based, or cell based; and/or the target cell/tissue. For proteins, methods of in vivo administration include parenteral administration, specifically including but not limited to, intravenous administration, intraperitoneal administration, intramuscular administration, intranodal administration, intracoronary administration, intraarterial administration (e.g., into a carotid artery), subcutaneous administration, intraarticular administration, intraventricular administration, and direct injection into a tissue. Combinations of routes of delivery can be used and in some instances, may enhance the therapeutic effects of the composition.

Many of the above-described routes of administration, including intravenous, intraperitoneal, intradermal, and intramuscular administrations can be performed using methods standard in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred patients to protect include humans.

Each reference described and/or cited herein is incorporated by reference in its entirety.

The following examples are provided for the purpose of illustration and are not intended to limit the scope of the present invention.

TABLE 1

| Designation | Target groups | Molecular weight (daltons) |
|---|---|---|
| ME-200MA0B | —SH | 20,000 |
| ME-020MA | —SH | 2,000 |
| ME-400MA | —SH | 40,000 |
| GL2-400MA | —SH | 40,000 |
| GL4-400MA | —SH | 40,000 |
| GL2-800MA | —SH | 80,000 |
| ME-050GS | —NH$_2$, —OH, —OH | 5,000 |
| ME-200GS | —NH$_2$, —OH, —SH | 20,000 |

TABLE 1-continued

| Designation | Target groups | Molecular weight (daltons) |
|---|---|---|
| ME-200AL | —NH$_2$ | 20,000 |
| MEPA-20T | —COOH | 20,000 |

EXAMPLES

Example 1

Production of Truncated CBS Protein in Bacteria a. Recombinant Expression of Truncated CBS Protein in Bacteria A truncated human CBS variant lacking specific portions of the non-conserved regions (r-hCBSΔC; SEQ ID No: 3) was constructed and over-expressed using the previously described E. coli based expression system (Kozich and Kraus, 1992, supra Constructs encoding the truncated human CBS protein variant r-hCBSΔC (SEQ ID NO: 4) were generated by a modification of the previously described pHCS3 CBS expression construct (Kozich and Kraus, 1992, Hum. Mutat. 1:113-123) which contains the CBS full-length coding sequence (SEQ ID NO: 1) cloned into pKK388.1. To generate C-terminal deletion constructs, CBS cDNA fragments spanning the desired nucleotide residues were amplified using primers incorporating Sph I and Kpn I sites to the 5' and 3' respective ends of the PCR product. All PCR products were then cut with Sph I and Kpn I and cloned by ligation into the pHCS3 vector digested with Sph I and Kpn I. An Sph I site naturally occurs in the CBS cDNA, just upstream of the antisense primer hybridization site (base pair position 1012, according to the CBS cDNA numbering SEQ ID NO: 1). PCR products thus generated were then digested with Nco I and Sph I and ligated into the pHCS3 plasmid cut with the same enzymes.

```
pKK CBS Δ414-551
Sense:
                                          (SEQ ID NO: 5)
CGTAGAATTCACCTTTGCCCGCATGCTGAT
(SphI restriction site in bold)

Antisense:
                                          (SEQ ID NO: 6)
TACGGGTACCTCAACGGAGGTGCCACCACCAGGGC
(KpnI restriction site in bold)
```

Finally, the construct was transformed into E. coli BL21 (Stratagene). The authenticity of the construct was verified by DNA sequencing using a Thermo Sequenase Cy5.5 sequencing kit (Amersham Pharmacia Biotech) and the Visible Genetics Long-Read Tower System-V3.1 DNA sequencer according to the manufacturer's instructions.

For bacterial expression analysis of CBS deletion mutants, growth of E. coli BL21 cells bearing the CBS truncation mutant construct, induction of expression and the generation of crude cell lysates were performed as described previously (Maclean et al., 2002, Hum. Mutat. 19:641-55).

An alternative method was also employed to make a sequence-optimized, truncated human CBS enzyme (r-hCBSΔC; SEQ ID No: 3) in a pET28a (+) vector. The full length (551 aa) human CBS coding sequence was optimized for bacterial expression and cloned into the pUC57 vector following digestion with the EcoRV restriction enzyme, by GenScript USA Inc. (NJ, USA). The CBS sequence was then amplified by PCR using primers A1 and A2 to generate a sequence coding for the truncated enzyme (aa 1-413):

Primers:

```
A1
                                          (SEQ ID NO: 7)
5'agtcgcCCATGGcgtcagaaacccccgcag 3'
NcoI restriction site in CAPs.
Bold G mutated to C (for proline).

A2
                                          (SEQ ID NO: 8)
5'atcgcgCTCGAGttagcgcaggtgccaccac 3'
XhoI restriction site in CAPs,
followed by TTA for stop codon
```

The PCR product was then digested with the restriction enzymes NcoI and XhoI, and ligated into the pET-28a(+) vector (commercially available from EMD Millipore, Billerica, Mass.) that was digested with the same enzymes. Cloning into the optimal NcoI site of pET-28a(+) results in a G→C mutation as compared to the CBS wild-type sequence (coding for alanine instead of proline). Accordingly, a Site-Directed Mutagenesis kit (Stratagene, Calif., USA) utilizing primers B1 and B2 was used to re-generate the wild type sequence to code for proline:

```
B1
                                          (SEQ ID NO: 9)
5'GGAGATATACCATGCCGTCAGAAACCCCGC 3'

B2
                                          (SEQ ID NO: 10)
5'GCGGGGTTTCTGACGGCATGGTATATCTCC 3'
```

The full sequence of the optimized, truncated human CBS enzyme was then verified by sequencing.

Expression of the truncated CBS is controlled by the upstream T7 promoter in the pET-28a(+) vector, and requires transformation into DE3 bacteria and induction by IPTG.

b. Expression of the Sequence-Optimized, Truncated Human CBS Enzyme

The pET-28a(+) vector, harboring the sequence coding for the truncated human CBS, was transformed into DE3 bacteria, i.e., HMS174(DE3), and kanamycin-resistant clones were selected and maintained as stock glycerol at −80° C. for further use.

Bacteria from stock glycerol was grown in 5 ml of Luria-Bertani (LB) medium, containing 30 ug/ml kanamycin, overnight at 37° C. on a rotational shaker at 275 RPM. The next morning, 1 ml of the overnight culture was added to a 100 ml Terrific Broth (TB) medium containing 30 ug/ml kanamycin and grown overnight as described above. 10 ml of the overnight culture was then added to a 1 liter TB medium containing the following supplements:

0.001% of thiamine-HCl pH 8.0
0.0025% of pyridoxine-HCl pH 8.0
0.3 mM δ-(aminolevulinic acid) (δ-ALA) pH 8.0
150 µM ferric chloride
30 ug/ml of kanamycin The 1 liter culture was then grown at 30° C. on a rotational shaker at 275 RPM until OD$_{600}$ reached the value of ~0.6-0.7 and protein expression was induced by addition of 1 mM IPTG. Fermentation was continued for additional 16 hours. Cells were then harvested by a 10 minutes, 6000 RCF centrifugation at 4° C., washed with ice-cold 0.9% NaCl, re-centrifuged as above, and frozen at −80° C.

An aliquot, 4.45 ml of lysis buffer (20 mM NaH$_2$PO$_4$, pH=7.2, 40 mM NaCl, 0.1 mM PLP) per 1 gram of pellet, was then added to the cell pellet and the latter was homogenized in a Dounce homogenizer until no cells aggregates were visible. The homogenate was then treated with lysozyme (2 mg/ml final), incubated for 1 hour at 4° C. on a rocking platform, sonicated to reduce viscosity, and centrifuged at 53000 RCF. The supernatant, comprising the soluble fraction was then stored at −80° C.

Expression levels were verified by gel-electrophoresis followed by Coomassie gel staining, and specific activity was determined by the radioactive activity assay.

c. CBS Assay

CBS activity was determined by a previously described radioisotope assay using [$^{14}$C] serine as the labeled substrate (Kraus, 1987, *Methods Enzymol.* 143, 388-394). Protein concentrations were determined by the Lowry procedure (Lowry et al., 1951, *J Biol. Chem.* 193, 265-275) using bovine serum albumin (BSA) as a standard. One unit of activity is defined as the amount of CBS that catalyzes the formation of 1 μmol of cystathionine in 1 h at 37° C.

d. Denaturing and Native Polyacrylamide Gel Electrophoresis and Western Blotting Western blot analysis of crude cell lysates under both denaturing and native conditions was performed as described previously (Majtan et al., 2010 *J Biol. Chem.* 2010; 285(21): 15866-73) with some modifications. Soluble fractions of *E. coli* lysates containing the expressed mutant protein were mixed with sample buffer and run on a 6% native PAGE without a stacking gel. The final composition of the sample buffer was: 50 mM Tris-HCl, pH 8.9, 1 mM DTT, 10% glycerol, 0.001% bromphenol blue. Detection of heme was performed using a previously described method that relies on heme peroxidase activity (Vargas et al., 1993, *Anal. Biochem.* 209: 323-6).

e. Densitometric Scanning Analysis

Quantitative densitometry analysis was performed using the Imagemaster ID (version 2.0) software (Pharmacia). To construct a calibration curve, 50, 75, 100, 250, 500 and 1000 ng of purified wild type CBS protein were run on an SDS-PAGE together with crude cell lysates of the individual mutants. Following electrophoresis, Western blot immunoanalysis was conducted using rabbit anti-CBS serum. The signals corresponding to the experimentally observed CBS mutant subunits were all within the linear range of the calibration curve constructed with purified human CBS.

f. Determination of Plasma Metabolites

Stable-Isotope-Dilution Liquid Chromatography-Mass Spectrometry method was used to measure levels of sulfur amino acid metabolism compounds in mouse plasma, substantially as disclosed in Allen et al., 1993, Serum betaine N,N-dimethylglycine and N-methylglycine levels in patients with cobalamin and folate deficiency and related inborn errors of metabolism, *Metabolism* 42: 1448-1460.

Example 2

Plasma Retention Time In Vivo and Enzymatic Activity In Vitro are Enhanced Following rhCBSΔC PEGylation Once administered to patients, the rhCBSΔC enzyme was expected to be active in circulation in the blood. CBS enzyme activity was assayed as set forth in Example 1 and found to decrease when incubated in plasma in vitro at 37° C. (40% and 20% of activity following 24 h and 48 h incubation, respectively) as shown in FIG. 1b.

In order to confirm that the loss of activity observed in vitro also occurred in vivo, experiments were performed where C57BL/6J mice were injected with 5 mg/kg body weight of the rhCBSΔC via intra-peritoneal (IP), intra-vascular (IV) or sub-cutaneous (SQ) routes. To avoid excessive bleeding, two experimental groups (denoted 1 and 2) of five mice each were used for each injection route (total n=30). For each injection route, blood was collected from group 1 at 0, 1, 8 and 24 hours post injection and from group 2 at 1, 4, 10, and 48 hours post injection. Animals were bled by a single-use lancet for sub-mandibular bleeding and blood was collected into Capiject T-MLHG lithium heparin (12.5 IU) tubes with gel (Terumo Medical Corporation, NJ, USA). Tubes were then centrifuged at 1200 G for 10 min, followed by collection of plasma to 1.5 ml tubes and storage at −80° C.

Plasma was analyzed for CBS activity using the radiometric activity assay set forth in Example 1. CBS enzyme activity for the injected enzyme at the indicated time-points is shown in FIG. 1a. For the IP and IV routes, the peak activity was recorded 1 h post injection, whereas for the SQ route, activity peaked at 4 h post injection, due to the slower release from the SQ compartment to the circulation. Interestingly, 8-10 hours post injection, the activity was comparable for all injection routes with almost no activity at 24-48 hours post injection.

To monitor whether rhCBSΔC clearance from circulation may contribute to the rapid loss of activity in vivo as shown above, plasma proteins from two representative mice from each group described above were resolved by electrophoresis, transferred onto a PVDF membrane and reacted with an anti-human CBS antibody to follow CBS clearance from circulation. As shown in FIG. 1b, gradual clearance of the rhCBSΔC from circulation occurs as a function of time post injection, with no enzyme detected as early as 24 h post injection. Accordingly, clearance of the rhCBSΔC contributes to the observed rapid loss of activity in vivo.

rhCBSΔC enzyme was modified by polyethylene glycol (PEG) molecules (PEGylated) with ME-020MA or GL4-400MA PEGs. Polyethylene glycol was purchased from the NOF corporation (Tokyo, Japan). PEGylation was carried out according to the manufacturer's instructions. For example, coupling of PEG maleimide derivatives to the SH groups of CBS (5 mg/ml) was carried out in a 100 mM phosphate buffer pH=6 overnight at 4° C. Molar ratio of PEG molecules to the CBS protein was 10:1 or 5:1, depending on the PEG molecule.

PEGylated rhCBSΔC enzyme modified with ME-020MA or GL4-400MA PEGs was incubated in mouse plasma at 37° C. (final concentration 160 ng/μl), to determine whether such modification of the rhCBSΔC enzyme improved its stability. PEGylated rhCBSΔC enzyme activity was assayed by taking samples from mice administered PEGylated rhCBSΔC enzyme as set forth above at time points indicated in FIG. 1c and activity was compared to non-PEGylated enzyme using the radiometric activity assay set forth above. As shown in FIG. 1c, both the PEGylated and the non-PEGylated forms exhibited a decrease in activity as a function of incubation time, however, CBS activity was higher for the PEGylated enzymes.

To evaluate the activity of the PEGylated rhCBSΔC in vivo, C57BL/6J mice were injected with 5 mg/kg body weight of ME020MA- or GL4-400MA-PEGylated rhCBSΔC or with non-PEGylated rhCBSΔC via SQ route. Each treatment arm consisted of two groups of five mice (total 30 mice) and bled as described in above. Plasma was analyzed for CBS activity using the radiometric activity assay set forth in Example 1. Significant activity was detected for the two forms of the PEGylated enzyme 24 h and 48 h post injection, with GL4-400MA PEGylated rhCBSΔC activity peaking at 24 h, as shown in FIG. 1d. This was in sharp contrast to non-PEGylated rhCBSΔC, demonstrating low or no activity at these same time points. These results indicated that PEGylation of the rhCBSΔC enzyme was effective in prolonging its activity both in vitro and in vivo.

Example 3

Repeated Injection Regimen with PEGylated, but not with Non-PEGylated rhCBSΔC, Exhibited Buildup of CBS Activity In Vivo Rapid clearance rate of a protein from the circulation may be bypassed by increasing the number of injections to maintain higher plasma concentrations. Accordingly, a repeated injection regimen was tested with both non-PEGylated and PEGylated rhCBSΔC. C57BL/6J mice were injected at 0, 24, 48 hours (arrows in FIG. 2) with 5 mg/kg body weight of non-PEGylated rhCBSΔC (n=5) or with GL4-400MA rhCBSΔC (n=5) and bled at the indicated time points. Plasma was analyzed for CBS activity using the radiometric activity assay set forth in Example 1. As shown in FIG. 2, repeated injections of non-PEGylated enzyme failed to improve activity of the enzyme in circulation, resulting in nearly no activity 24 h after each injection. The latter finding is in sharp contrast to the activity of the PEGylated enzyme that peaked after two injections, before reaching a plateau. Thus, effective rhCBSΔC enzyme replacement therapy for homocystinuria requires PEGylation of the enzyme in order to maintain sufficient levels of the enzyme in the circulation.

Example 4

Single Injection of the PEGylated rhCBSΔC Reduced Homocysteine and Increased Cystathionine in Plasma The preceding Examples were carried out in wild-type mice and were focused on characterization of the clearance and activity of the injected rhCBSΔC, and comparison between the PEGylated and the non-PEGylated enzyme. Once established that PEGylation was necessary, a varied repertoire of PEGylated CBS enzyme molecules were first tested in wild-type mice, and were then evaluated in a mouse model of homocystinuria.

A repertoire of rhCBSΔC enzymes modified with various PEG molecules were tested in wild-type mice in order to determine the best PEGylation strategy. Twenty seven C57BL/6J mice were divided into nine experimental groups (n=3). Each experimental group was injected via SQ route with 5 mg/kg body weight of rhCBSΔC PEGylated with the PEG molecule indicated in FIG. 3, or injected with non-PEGylated enzyme. Blood samples were drawn at the time points indicated in FIG. 3 and the PEGylated rhCBSΔC activity determined using the radiometric activity assay set forth in Example 1. Data is presented in FIG. 3A as a histogram with standard deviation (STD), and as a scatter plot. Generally, PEGylation with polyethylene molecules of higher molecular weights (GL2800MA, 80 kDa; ME-400MA and GL2-400MA, 40 kDa; and ME200-MA0B, 20 kDa) were superior to PEGylation with molecules that were less than 20 kDa in size, and PEGylation using chemistry that targeted cysteine residues (denoted by "MA" to indicate the use of a maleimide reactive group) were superior over those utilizing different chemistries.

Before proceeding with studies on HO mice, daily fluctuations in homocysteine, cystathionine, cysteine and methionine in these mice were assayed to determine the best time of day for injection of the rhCBSΔC enzyme. Accordingly, blood from six HO mice was drawn at the time points indicated in FIG. 3B throughout a 24 h cycle and plasma metabolites levels were determined for each time point. As shown in FIG. 3B, levels of cystathionine, methionine and cysteine were largely constant throughout a 24 h cycle. Homocysteine levels, however, fluctuated greatly, with the highest concentration observed at 7:00 and the lowest at 15:00 hours. Accordingly, 15:00 (3 pm) was selected as the ideal time for injections and bleedings.

rhCBSΔC molecules PEGylated with ME-400MA (lane 1, FIG. 3C), GL4-400MA (lane 2) or ME-200MA0B (lane 3) were resolved by electrophoresis along with the non-PEGylated enzyme (lane 4), and stained with Coomassie blue. The S.A. for each of the PEGylated and non-PEGylated rhCBSΔC is indicated in the table accompanying FIG. 3C. As shown, PEGylation had no effect on S.A. values, and the enzyme remained as active as it was prior to PEGylation. As shown in the gel, PEGylation of rhCBSΔC under the conditions used in this experiment produced di-, and tri-pegylated rhCBSΔC enzyme.

The overall goal of the experiments described herein was to test the ability of the rhCBSΔC to lower homocysteine and increase cystathionine in vivo in order to be used as enzyme replacement therapy (ERT) for homocystinuria. The HO mice model for homocystinuria was used to test the potential of the rhCBSΔC to serve in ERT. HO mice were injected once with rhCBSΔC that was PEGylated with the PEG molecules (GL4-400MA, ME-400MA, ME-200MA0B) indicated in FIGS. 3D and 3E at time 0, and bled at times 0 (prior to injection), 24, 48 and 72 hours post injection. Levels of plasma homocysteine (FIG. 3D) and cystathionine (FIG. 3E) for each of the groups (n=5-6) are indicated. As shown in FIG. 3D, homocysteine levels decreased significantly for each PEGylated form used, and cystathionine levels (FIG. 3E) increased about 6 to 7-fold compared to time 0. Thus, administration of a PEGylated rhCBSΔC was found to significantly and positively impact homocysteine and cystathionine levels in vivo.

Example 5

Repeated Injection of the PEGylated rhCBSΔC Significantly Impacted Homocysteine and Cystathionine Plasma Levels, and Restored Normal Cysteine Levels A long term, repeated injection regimen, comparing non-PEGylated and PEGylated enzyme for the ability to reduce and maintain low levels of homocysteine as well as to increase cystathionine and cysteine levels was conducted as follows. Six HO mice were injected (arrows, FIG. 4) with the rhCBSΔC PEGylated with GL4-400MA PEG, on days 0, 1, 2, 3 and 4, and then again on days 14, 15, 16, 17 and 18. Plasma samples were drawn (always prior to injection) at the time points indicated in FIG. 4. For comparison, same injection regimen was carried out in five HO mice injected with the non-PEGylated enzyme. The levels of plasma metabolites were determined by Stable-Isotope-Dilution Liquid Chromatography-Mass Spectrometry as described in Example 1f. Homocysteine (results shown in FIG. 4a) and cystathionine (FIG. 4b) plasma concentrations for each of the experimental HO mouse are indicated. Average values for homocysteine and cystathionine for each experimental group are presented as well (in FIG. 4c). As shown in FIGS. 4a-4c, average homocysteine concentrations decreased in 48 h from 182 μM to 38 μm and stayed low for the entire week. Cystathionine reached a concentration of 42 μM at 48 h, from the initial 4.7 μm at time 0, and remained high during the first week. During the washout period, metabolites returned to their initial values. Subsequent CBS injections led again to a sharp drop in homocysteine levels and a rise in cystathionine levels.

The effects of PEGylated rhCBSΔC on plasma homocysteine levels as compared to non-PEGylated rhCBSΔC was also determined, as presented in FIG. 4d as percentage of time 0. FIG. 4d illustrates that, in contrast to PEGylated rhCBSΔC, the non-PEGylated enzyme had no effect on homocysteine concentration. This is in agreement with the results shown in Examples 2 and 3 showing that the non-PEGylated enzyme is rapidly cleared from circulation with no indication of significant activity 24 h and 48 h post injection.

The effects of PEGylated rhCBSΔC on plasma cysteine levels as compared to the non-PEGylated rhCBSΔC was also determined using the same experimental methods. As shown in FIG. 4E, cysteine levels normalized (doubled as compared to time 0) during the injection period of the PEGylated enzyme, while no change in cysteine levels was observed using the non-PEGylated enzyme.

These results showed that PEGylated rhCBSΔC enzyme administered SQ to HO mice, significantly and positively affected homocysteine and cystathionine concentrations, and at the same time restored cysteine levels to their normal values. The latter experimental result is an indication that the intracellular transsulfuration pathway was activated following administration of rhCBSΔC.

TABLE 2

CBS Sequences

| Molecule | SEQ ID NO | Sequence |
|---|---|---|
| Human CBS nucleic acid sequence (full length) | 1 | atgccttctgagaccccccaggcagaagtggggcccacaggctgccc ccaccgctcagggccacactcggcgaaggggagcctggagaaggggt ccccagaggataaggaagccaaggagcccctgtggatccggcccgat gctccgagcaggtgcacctggcagctgggccggcctgcctccgagtc cccacatcaccacactgccccggcaaaatctccaaaaatcttgccag atattctgaagaaaatcggggacacccctatggtcagaatcaacaag attgggaagaagttcggcctgaagtgtgagctcttggccaagtgtga gttcttcaacgcgggcgggagcgtgaaggaccgcatcagcctgcgga tgattgaggatgctgagcgcgacgggacgctgaagcccgggacacg attatcgagccgacatccgggaacaccgggatcgggctggccctggc tgcggcagtgaggggctatcgctgcatcatcgtgatgccagagaaga tgagctccgagaaggtggacgtgctgcgggcactggggctgagatt gtgaggacgcccaccaatgccaggttcgactccccggagtcacacgt gggggtggcctggcggctgaagaacgaaatccccaattctcacatcc tagaccagtaccgcaacgccagcaacccccctggctcactacgacacc accgctgatgagatcctgcagcagtgtgatgggaagctggacatgct ggtggcttcagtgggcacgggcggcaccatcacgggcattgccagga agctgaaggagaagtgtcctggatgcaggatcattggggtggatccc gaagggtccatcctcgcagagccggaggagctgaaccagacggagca gacaacctacgaggtggaagggatcggctacgacttcatccccacgg tgctggacaggacggtggtggacaagtggttcaagagcaacgatgag gaggcgttcacctttgcccgcatgctgatcgcgcaagaggggctgct gtgcggtggcagtgctggcagcacggtggcggtggccgtgaaggctg cgcaggagctgcaggagggccagcgctgcgtggtcattctgcccgac tcagtgcggaactacatgaccaagttcctgagcgacaggtggatgct gcagaagggctttctgaaggaggaggacctcacggagaagaagccct ggtggtggcacctccgtgttcaggagctgggcctgtcagccccgctg accgtgctcccgaccatcacctgtgggcacaccatcgagatcctccg ggagaagggcttcgaccaggcgcccgtggtggatgaggcggggtaa tcctgggaatggtgacgcttgggaacatgctctcgtccctgcttgcc gggaaggtgcagccgtcagaccaagttggcaaagtcatctacaagca gttcaaacagatccgcctcacggacacgctgggcaggctctcgcaca tcctggagatggaccacttcgccctggtggtgcacgagcagatccag taccacagcaccgggaagtccagtcagcggcagatggtgttcggggt ggtcaccgccattgacttgctgaacttcgtggccgcccaggagcggg accagaagtga |
| Human CBS polypeptide Sequence (full length enzyme) | 2 | MPSETPQAEVGPTGCPHRSGPHSAKGSLEKGSPEDKEAKEPLWIRPD APSRCTWQLGRPASESPHHHTAPAKSPKILPDILKKIGDTPMVRINK IGKKFGLKCELLAKCEFFNAGGSVKDRISLRMIEDAERDGTLKPGDT IIEPTSGNTGIGLALAAAVRGYRCIIVMPEKMSSEKVDVLRALGAEI VRTPTNARFDSPESHVGVAWRLKNEIPNSHILDQYRNASNPLAHYDT TADEILQQCDGKLDMLVASVGTGGTITGIARKLKEKCPGCRIIGVDP EGSILAEPEELNQTEQTTYEVEGIGYDFIPTVLDRTVVDKWFKSNDE EAFTFARMLIAQEGLLCGGSAGSTVAVAVKAAQELQEGQRCVVILPD SVRNYMTKFLSDRWMLQKGFLKEEDLTEKKPWWWHLRVQELGLSAPL TVLPTITCGHTIEILREKGFDQAPVVDEAGVILGMVTLGNMLSSLLA GKVQPSDQVGKVIYKQFKQIRLTDTLGRLSHILEMDHFALVVHEQIQ YHSTGKSSQRQMVFGWTAIDLLNFVAAQERDQK |
| Polypeptide Sequence of r-hCβSΔC (recombinant human carboxy-truncated CBS) | 3 | MPSETPQAEVGPTGCPHRSGPHSAKGSLEKGSPEDKEAKEPLWIRPD APSRCTWQLGRPASESPHHHTAPAKSPKILPDILKKIGDTPMVRINK IGKKFGLKCELLAKCEFFNAGGSVKDRISLRMIEDAERDGTLKPGDT IIEPTSGNTGIGLALAAAVRGYRCIIVMPEKMSSEKVDVLRALGAEI VRTPTNARFDSPESHVGVAWRLKNEIPNSHILDQYRNASNPLAHYDT TADEILQQCDGKLDMLVASVGTGGTITGIARKLKEKCPGCRIIGVDP EGSILAEPEELNQTEQTTYEVEGIGYDFIPTVLDRTVVDKWFKSNDE EAFTFARMLIAQEGLLCGGSAGSTVAVAVKAAQELQEGQRCVVILPD SVRNYMTKFLSDRWMLQKGFLKEEDLTEKKPWWWHLR |

TABLE 2-continued

CBS Sequences

| Molecule | SEQ ID NO | Sequence |
|---|---|---|
| Nucleic acid sequence of r-hCβSΔC | 4 | atgccgtcagaaaccccgcaggcagaagtgggtccgacgggttgcccgcac cgtagcggtccgcattctgcaaaaggcagtctggaaaaaggttccccggaa gataaagaagccaaagaaccgctgtggattcgtccggacgcaccgtcacgc tgtacctggcagctgggtcgtccggcaagcgaatctccgcatcaccatacg gctccggcgaaaagtccgaaaattctgccggatatcctgaagaaaattggt gacaccccgatggttcgtatcaacaaaatcggcaaaaaattcggtctgaaa tgcgaactgctggctaaatgtgaattttcaatgcgggcggttccgtgaaa gatcgtatctcactgcgcatgattgaagatgctgaacgcgacggcaccctg aaaccgggtgatacgattatcgaaccgacctctggcaacacgggtatcggt ctggcactggcggcggcagtccgtggttatcgctgcattatcgtgatgccg gaaaaaatgagctctgaaaaagttgatgtcctgcgtgctctgggcgcggaa attgttcgtaccccgacgaatgcccgcttcgacagtccggaatcccatgtg ggtgttgcatggcgcctgaaaaacgaaatcccgaattcgcacattctggat cagtatcgtaacgctagcaatccgctggcgcattacgataccacggccgac gaaatcctgcagcaatgtgatggcaaactggacatgctggtcgcttctgtg ggtaccggcggtaccattacgggcatcgcgcgtaaactgaaagaaaaatgc ccgggctgtcgcattatcggtgtggatccggaaggcagtattctggcggaa ccggaagaactgaaccagaccgaacaaaccacgtatgaagttgaaggcatc ggttacgattttattccgaccgtcctggatcgcacggtggttgacaaatgg ttcaaaagcaatgacgaagaagcctttaccttcgcacgtatgctgatcgct caggaaggtctgctgtgcgcggtggttcagcaggttcgacggtcgcagtggca gttaaagctgcgcaggaactgcaagaaggtcaacgttgtgtcgtgattctg ccggattctgttcgcaactacatgaccaaatttctgagtgaccgttggatg ctgcaaaaaggcttcctgaaagaagaagatctgaccgagaaaaaaccgtgg tggtggcacctgcgctaa |

Having described the invention in detail and by reference to specific embodiments thereof, it will be apparent that modifications and variations are possible without departing from the scope of the invention defined in the appended claims.

More specifically, although some aspects of the present invention are identified herein as particularly advantageous, it is contemplated that the present invention is not necessarily limited to these particular aspects of the invention.

What is claimed:

1. A pharmaceutical composition comprising an isolated carboxyl-terminal truncated cystathionine-β-synthase (CBS) polypeptide comprising the amino acid sequence of SEQ ID NO: 2, wherein said CBS protein has a carboxyl-terminal truncation spanning any of amino acid residues 383-551 of SEQ ID NO: 2, that is covalently linked to at least one or a plurality of polyethylene glycol molecules.

2. The pharmaceutical composition of claim 1, wherein the isolated carboxyl-terminal truncated cystathionine-β-synthase polypeptide is a chemically cleaved or genetically engineered truncate comprising SEQ ID NO: 3 (r-hCBSΔC).

3. A method for reducing homocysteine in an individual in need thereof comprising administration of the pharmaceutical composition of claim 1.

4. The method of claim 3, wherein the pharmaceutical composition is administered by intravenous injection, subcutaneous injection, or intraperitoneal injection.

5. The method of claim 3, wherein the pharmaceutical composition is administered by subcutaneous injection.

6. The method of claim 3, wherein the pharmaceutical composition comprises an amount of r-hCBSΔC polypeptide wherein 0.1 mg/kg-20 mg/kg is administered.

7. A method for elevating cystathionine or cysteine, in an individual in need thereof comprising administration of the pharmaceutical composition of claim 1.

8. The method of claim 7, further comprising the administration of one or more of an anti-coagulant, a statin, or a relaxed protein restricted diet, anethole dithiolethione or betaine.

9. The method of claim 7, wherein the pharmaceutical composition is administered by intravenous injection, subcutaneous injection, or intraperitoneal injection.

10. The method of claim 7, wherein the pharmaceutical composition is administered by intravenous injection.

11. The method of claim 7, wherein the pharmaceutical composition comprises an amount of r-hCBSΔC polypeptide wherein up to 20 mg/kg is administered to an individual in need thereof.

12. A method for treating or ameliorating a disease, disorder, or condition, associated with elevated homocysteine, methionine, S-adenosylmethionine and S-adenosylhomocysteine and low cystathionine and cysteine levels comprising administering to an individual in need thereof a pharmaceutically effective amount of the pharmaceutical composition of claim 1.

13. The method of claim 12, wherein the disease, disorder, or condition associated with elevated homocysteine is mental retardation, osteoporosis, ectopia lentis, kyphoscoliosis, stroke, myocardial infarction, or pulmonary embolism.

14. The method of claim 12, wherein the pharmaceutical composition comprises an amount of r-hCBSΔC polypeptide wherein up to 20 mg/kg is administered by parenteral injection.

15. The method of claim 12, further comprising administration of anethole dithiolethione or betaine.

16. The method of claim 15, wherein betaine administration occurs twice daily.

17. A method for preventing a disease, disorder, or condition associated with elevated homocysteine, comprising administering to a patient in need thereof a pharmaceutically effective amount of the pharmaceutical composition of claim 1.

18. The method of claim 17, wherein the disease, disorder, or condition associated with elevated homocysteine is mental retardation, osteoporosis, ectopia lentis, kyphoscoliosis, stroke, myocardial infarction, or pulmonary embolism.

19. The method of claim 17, wherein the pharmaceutical composition comprises an amount of r-hCBSΔC polypeptide wherein up to 20 mg/kg is administered to an individual in need thereof.

20. The method of claim 17, further comprising administration of anethole dithiolethione or betaine.

21. The method of claim 20, wherein betaine administration occurs twice daily.

22. A pharmaceutical composition comprising the isolated carboxyl-terminal truncated human cystathionine-β-synthase (r-hCBSΔC) polypeptide of claim 1 that retains 70% or more of the initial activity of the administered composition after 24 hours.

23. The pharmaceutical composition of claim 1, wherein the isolated carboxyl-terminal truncated cystathionine-β-synthase polypeptide further comprises an amino-terminal truncation spanning any of amino acid residues 1-39 of SEQ ID NO: 2.

24. The pharmaceutical composition of claim 1, wherein the carboxyl-terminal truncation spans amino acid residues 401-551, 414-551, 442-551, 489-551, 497-551, 524-551 or 544-551 of SEQ ID NO: 2.

* * * * *

SEQUENCE LISTING

```
<160> NUMBER OF SEQ ID NOS: 10

<210> SEQ ID NO 1
<211> LENGTH: 1656
<212> TYPE: DNA
<213> ORGANISM: Homo sapiens

<400> SEQUENCE: 1
atgccttctg agaccccca  ggcagaagtg gggcccacag gctgccccca  ccgctcaggg    60
ccacactcgg cgaaggggag cctggagaag gggtccccag aggataagga agccaaggag   120
cccctgtgga tccggcccga tgctccgagc aggtgcacct ggcagctggg ccggcctgcc   180
tccgagtccc cacatcacca cactgccccg gcaaaatctc caaaaatctt gccagatatt   240
ctgaagaaaa tcggggacac ccctatggtc agaatcaaca agattgggaa gaagttcggc   300
ctgaagtgtg agctcttggc caagtgtgag ttcttcaacg cgggcgggag cgtgaaggac   360
cgcatcagcc tgcggatgat tgaggatgct gagcgcgacg gacgctgaa  gcccggggac   420 acgattatcg agccgacatc cgggaacacc gggatcgggc tggccctggc tgcggcagtg   480 agggctatc  gctgcatcat cgtgatgcca gagaagatga gctccgagaa ggtggacgtg   540
ctgcgggcac tgggggctga gattgtgagg acgcccacca atgccaggtt cgactccccg   600
gagtcacacg tgggggtggc ctggcggctg aagaacgaaa tcccaattc  tcacatccta   660 gaccagtacc gcaacgccag caaccccctg gctcactacg acaccaccgc tgatgagatc   720
ctgcagcagt gtgatgggaa gctggacatg ctggtggctt cagtgggcac gggcggcacc   780
atcacgggca ttgccaggaa gctgaaggag aagtgtcctg atgcaggat  cattggggtg   840 gatcccgaag ggtccatcct cgcagagccg gaggagctga accagacgga gcagacaacc   900
```

```
tacgaggtgg aagggatcgg ctacgacttc atccccacgg tgctggacag gacggtggtg    960
gacaagtggt tcaagagcaa cgatgaggag gcgttcacct ttgcccgcat gctgatcgcg   1020 caagagggc tgctgtgcgg tggcagtgct ggcagcacgg tggcggtggc cgtgaaggct   1080
gcgcaggagc tgcaggaggg ccagcgctgc gtggtcattc tgcccgactc agtgcggaac   1140
tacatgacca agttcctgag cgacaggtgg atgctgcaga agggctttct gaaggaggag   1200
gacctcacgg agaagaagcc ctggtggtgg cacctccgtg ttcaggagct gggcctgtca   1260
gccccgctga ccgtgctccc gaccatcacc tgtgggcaca ccatcgagat cctccgggag   1320
aagggcttcg accaggcgcc cgtggtggat gaggcggggg taatcctggg aatggtgacg   1380
cttgggaaca tgctctcgtc cctgcttgcc gggaaggtgc agccgtcaga ccaagttggc   1440
aaagtcatct acaagcagtt caaacagatc cgcctcacgg acacgctggg caggctctcg   1500
cacatcctgg agatggacca cttcgccctg gtggtgcacg agcagatcca gtaccacagc   1560
accgggaagt ccagtcagcg gcagatggtg ttcggggtgg tcaccgccat tgacttgctg   1620
aacttcgtgg ccgcccagga gcgggaccag aagtga                              1656
```

<210> SEQ ID NO 2
<211> LENGTH: 551
<212> TYPE: PRT
<213> ORGANISM: Homo sapiens

<400> SEQUENCE: 2

```
Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
    50                  55                  60

His His His Thr Ala Pro Ala Lys Ser Pro Lys Ile Leu Pro Asp Ile
65                  70                  75                  80

Leu Lys Lys Ile Gly Asp Thr Pro Met Val Arg Ile Asn Lys Ile Gly
                85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240
```

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
    370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg Val Gln Glu
                405                 410                 415

Leu Gly Leu Ser Ala Pro Leu Thr Val Leu Pro Thr Ile Thr Cys Gly
            420                 425                 430

His Thr Ile Glu Ile Leu Arg Glu Lys Gly Phe Asp Gln Ala Pro Val
        435                 440                 445

Val Asp Glu Ala Gly Val Ile Leu Gly Met Val Thr Leu Gly Asn Met
    450                 455                 460

Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
        515                 520                 525

Met Val Phe Gly Val Val Thr Ala Ile Asp Leu Leu Asn Phe Val Ala
    530                 535                 540

Ala Gln Glu Arg Asp Gln Lys
545                 550

<210> SEQ ID NO 3
<211> LENGTH: 413
<212> TYPE: PRT
<213> ORGANISM: Artificial Sequence
<220> FEATURE:
<223> OTHER INFORMATION: Synthetic

<400> SEQUENCE: 3

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45

Pro Ser Arg Cys Thr Trp Gln Leu Gly Arg Pro Ala Ser Glu Ser Pro
 50                  55                  60

His His His Thr Ala Pro Ala Lys Ser Pro Lys Ile Leu Pro Asp Ile
 65                  70                  75                  80

Leu Lys Lys Ile Gly Asp Thr Pro Met Val Arg Ile Asn Lys Ile Gly
                 85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
            115                 120                 125

Asp Ala Glu Arg Asp Gly Thr Leu Lys Pro Gly Asp Thr Ile Ile Glu
130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
            195                 200                 205

Arg Leu Lys Asn Glu Ile Pro Asn Ser His Ile Leu Asp Gln Tyr Arg
210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
            275                 280                 285

Glu Pro Glu Glu Leu Asn Gln Thr Glu Gln Thr Thr Tyr Glu Val Glu
290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
            355                 360                 365

Arg Cys Val Val Ile Leu Pro Asp Ser Val Arg Asn Tyr Met Thr Lys
370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg
                405                 410

<210> SEQ ID NO 4
<211> LENGTH: 1242
<212> TYPE: DNA
<213> ORGANISM: Artificial Sequence
<220> FEATURE:
<223> OTHER INFORMATION: Synthetic

<400> SEQUENCE: 4

```
atgccgtcag aaaccccgca ggcagaagtg ggtccgacgg gttgcccgca ccgtagcggt    60
ccgcattctg caaaaggcag tctggaaaaa ggttccccgg aagataaaga agccaaagaa   120
ccgctgtgga ttcgtccgga cgcaccgtca cgctgtacct ggcagctggg tcgtccggca   180
agcgaatctc cgcatcacca tacggctccg gcgaaaagtc cgaaaattct gccggatatc   240
ctgaagaaaa ttggtgacac cccgatggtt cgtatcaaca aaatcggcaa aaaattcggt   300
ctgaaatgcg aactgctggc taaatgtgaa tttttcaatg cgggcggttc cgtgaaagat   360
cgtatctcac tgcgcatgat tgaagatgct gaacgcgacg gcaccctgaa accgggtgat   420
acgattatcg aaccgacctc tggcaacacg ggtatcggtc tggcactggc ggcggcagtc   480
cgtggttatc gctgcattat cgtgatgccg gaaaaaatga gctctgaaaa agttgatgtc   540
ctgcgtgctc tgggcgcgga aattgttcgt accccgacga atgcccgctt cgacagtccg   600
gaatcccatg tgggtgttgc atggcgcctg aaaaacgaaa tcccgaattc gcacattctg   660
gatcagtatc gtaacgctag caatccgctg gcgcattacg ataccacggc cgacgaaatc   720
ctgcagcaat gtgatggcaa actggacatg ctggtcgctt ctgtgggtac cggcggtacc   780
attacgggca tcgcgcgtaa actgaaagaa aaatgcccgg gctgtcgcat tatcggtgtg   840
gatccggaag gcagtattct ggcggaaccg gaagaactga accagaccga acaaaccacg   900
tatgaagttg aaggcatcgg ttacgatttt attccgaccg tcctggatcg cacggtggtt   960
gacaaatggt tcaaaagcaa tgacgaagaa gcctttacct tcgcacgtat gctgatcgct  1020
caggaaggtc tgctgtgcgg tggttcagca ggttcgacgg tcgcagtggc agttaaagct  1080
gcgcaggaac tgcaagaagg tcaacgttgt gtcgtgattc tgccggattc tgttcgcaac  1140
tacatgacca aatttctgag tgaccgttgg atgctgcaaa aaggcttcct gaaagaagaa  1200
gatctgaccg agaaaaaacc gtggtggtgg cacctgcgct aa                    1242
```

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5

```
cgtagaattc acctttgccc gcatgctgat                                     30
```

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 6

```
tacgggtacc tcaacggagg tgccaccacc agggc                               35
```

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7

```
agtcgcccat ggcgtcagaa accccgcag                                      29
```

```
<210> SEQ ID NO 8
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 8
atcgcgctcg agttagcgca ggtgccacca c                              31

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 9
ggagatatac catgccgtca gaaaccccgc                                30

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 10
gcggggtttc tgacggcatg gtatatctcc                                30
```